United States Patent
Haskins

(10) Patent No.: US 10,918,762 B2
(45) Date of Patent: Feb. 16, 2021

(54) MAGNETIC PANTY LINER ASSEMBLY

(71) Applicant: Melissa Haskins, Craig, CO (US)

(72) Inventor: Melissa Haskins, Craig, CO (US)

( * ) Notice: Subject to any disclaimer, the term of this patent is extended or adjusted under 35 U.S.C. 154(b) by 400 days.

(21) Appl. No.: 15/925,201

(22) Filed: Mar. 19, 2018

(65) Prior Publication Data

US 2019/0282723 A1 Sep. 19, 2019

(51) Int. Cl.
*A61L 15/18* (2006.01)
*A61L 15/42* (2006.01)
*A61F 13/535* (2006.01)
*A61F 13/475* (2006.01)
*A61F 13/537* (2006.01)
*A61F 13/53* (2006.01)
*A61F 13/47* (2006.01)
*A61F 13/512* (2006.01)

(52) U.S. Cl.
CPC ............ *A61L 15/18* (2013.01); *A61F 13/475* (2013.01); *A61F 13/535* (2013.01); *A61F 13/53743* (2013.01); *A61L 15/42* (2013.01); *A61F 2013/4708* (2013.01); *A61F 2013/530029* (2013.01); *A61F 2013/530036* (2013.01)

(58) Field of Classification Search
CPC .. A61F 13/4756; A61F 13/475; A61F 13/535; A61F 13/4752; A61F 13/51104; A61F 13/51108; A61F 13/5126; A61F 13/5121; A61F 13/512; A61F 2013/5113; A61F 2013/530036; A61F 2013/530029; A61F 2013/53773; A61F 13/51105
See application file for complete search history.

(56) References Cited

U.S. PATENT DOCUMENTS

| | | | |
|---|---|---|---|
| 4,988,344 A | 1/1991 | Reising | |
| 5,368,909 A | 11/1994 | Langdon | |
| 8,535,287 B2 | 9/2013 | Sulger | |
| 2003/0093043 A1 | 5/2003 | Yi et al. | |
| 2008/0195068 A1* | 8/2008 | Kao | A61F 13/4756 604/361 |
| 2010/0036350 A1* | 2/2010 | Heo | A61L 15/18 604/385.01 |
| 2012/0157952 A1* | 6/2012 | Poruthoor | A61L 15/42 604/372 |
| 2016/0074237 A1* | 3/2016 | Rosati | A61F 13/15699 156/219 |
| 2017/0354550 A1* | 12/2017 | Park | A61F 13/5116 |
| 2018/0049929 A1* | 2/2018 | Konawa | A61F 13/51104 |

* cited by examiner

*Primary Examiner* — Tatyana Zalukaeva
*Assistant Examiner* — Heather K Barnwell

(57) ABSTRACT

A magnetic panty liner assembly for reducing menstrual pain includes a first panel, a first panel, a second panel, and a third panel. The second panel, which is absorbent, is coupled to a lower face of the first panel. The third panel is coupled to a bottom surface of the second panel and a perimeter of the first panel to enclose the second panel. The ridge and the third panel are impermeable. A coupler on an exterior face of the third panel is configured to couple the third panel to an undergarment. Menstrual fluid flows through the first panel to be absorbed by the second panel. A ridge on the first panel is positioned in abutment to skin of the user to prevent leakage. Magnets that are positioned between the second panel and the third panel are configured to reduce pain of menstruation.

16 Claims, 4 Drawing Sheets

MAGNETIC PANTY LINER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to panty liner assemblies and more particularly pertains to a new panty liner assembly for reducing menstrual pain.

BRIEF SUMMARY OF THE INVENTION

An embodiment of the disclosure meets the needs presented above by generally comprising a first panel, a second panel, and a third panel. The second panel, which is absorbent, is coupled to a lower face of the first panel. The third panel is coupled to a bottom surface of the second panel and a perimeter of the first panel to enclose the second panel. The ridge and the third panel are impermeable. A coupler on an exterior face of the third panel is configured to couple the third panel to an undergarment. Menstrual fluid flows through the first panel to be absorbed by the second panel. A ridge on the first panel is positioned in abutment to skin of the user to prevent leakage. Magnets that are positioned between the second panel and the third panel are configured to reduce pain of menstruation.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
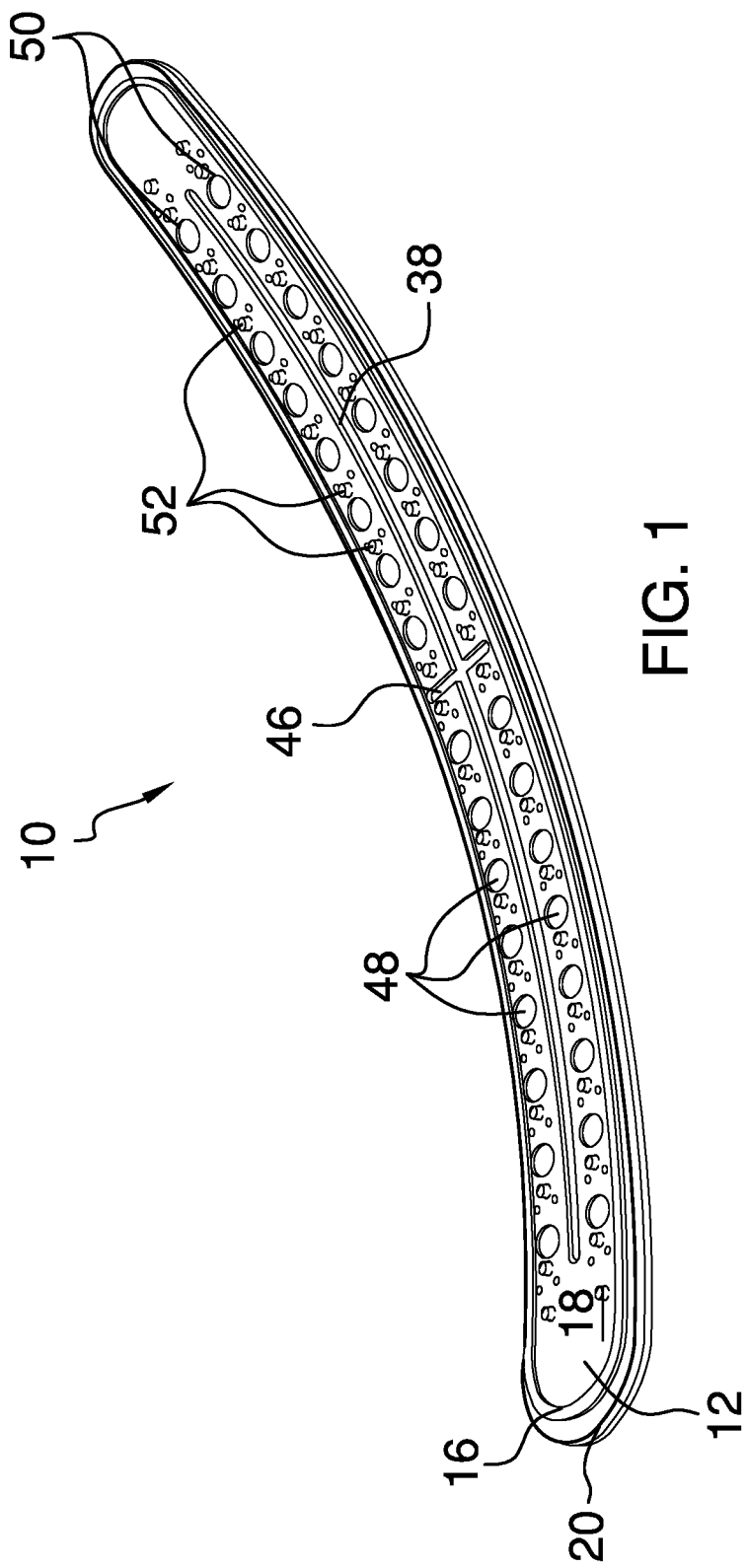
FIG. 1 is an isometric perspective view of a magnetic panty liner assembly according to an embodiment of the disclosure.

With reference now to the drawings, and in particular to FIGS. 1 through 5 thereof, a new panty liner assembly embodying the principles and concepts of an embodiment of the disclosure and generally designated by the reference numeral 10 will be described.

Figure 2:
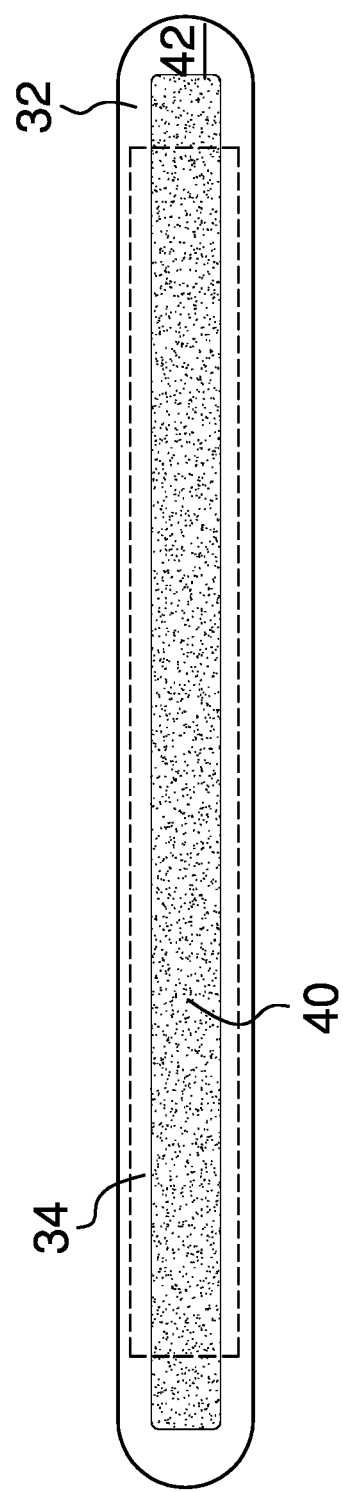
FIG. 2 is a bottom view of an embodiment of the disclosure.
Figure 3:
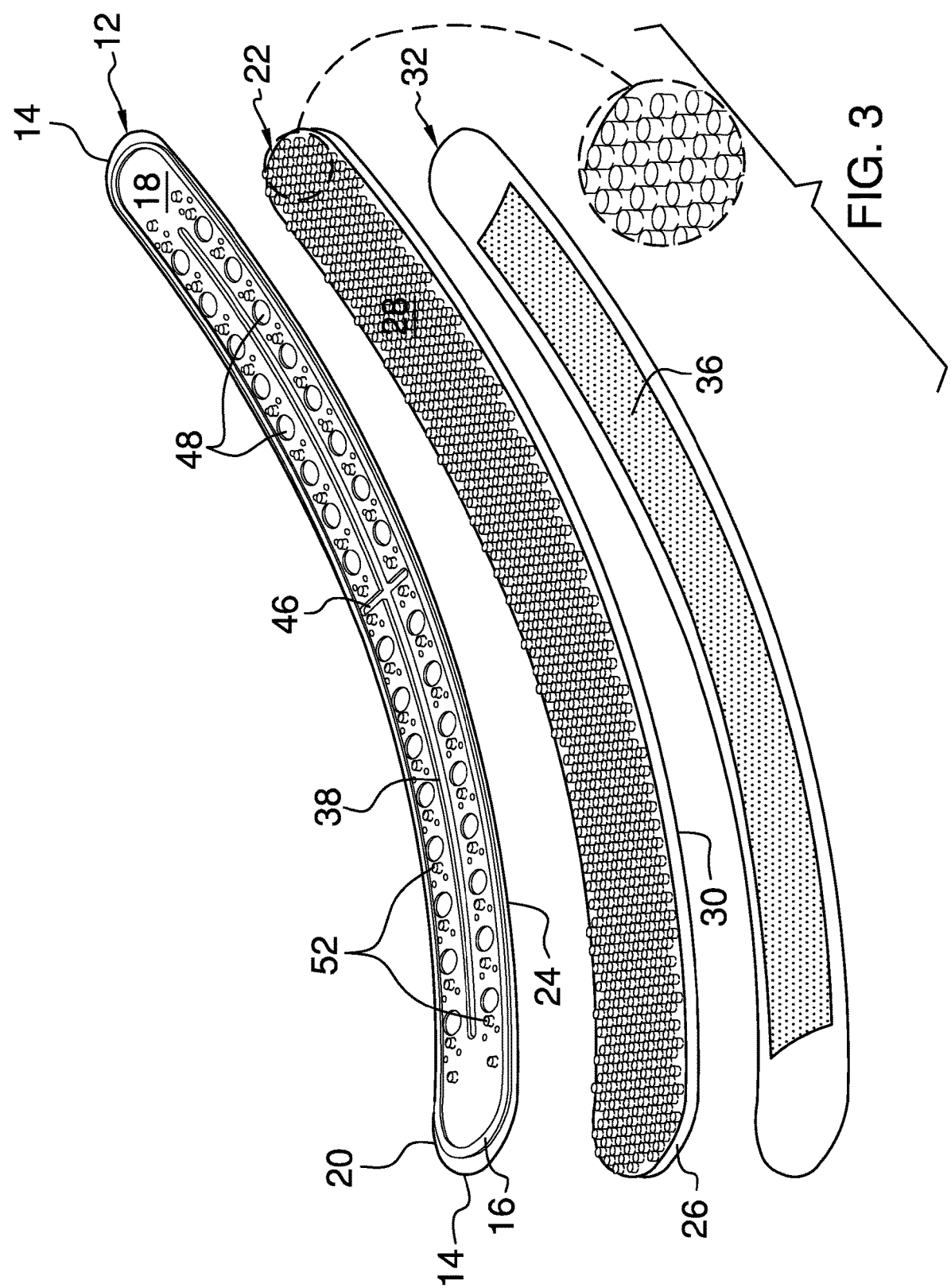
FIG. 3 is an exploded view of an embodiment of the disclosure.
Figure 4:
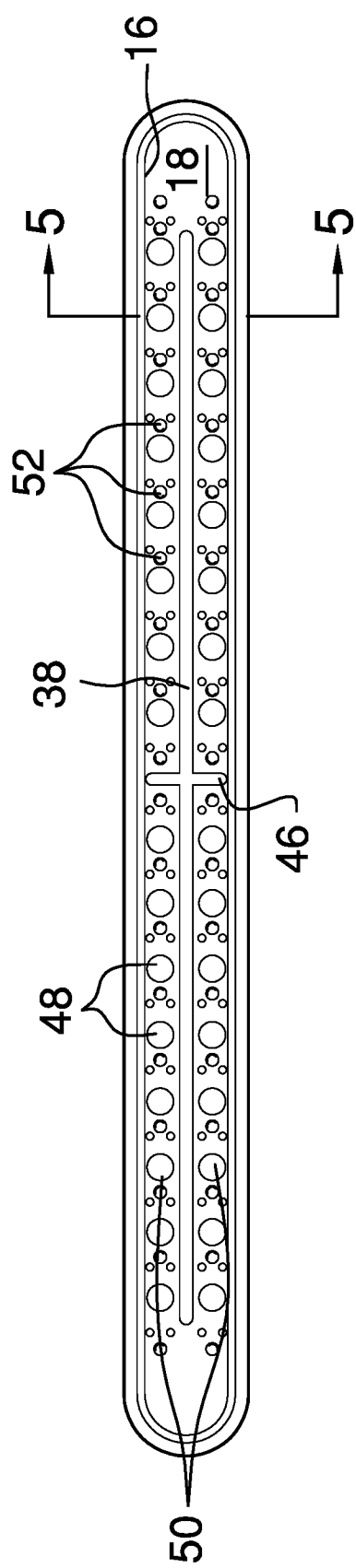
FIG. 4 is a top view of an embodiment of the disclosure.
Figure 5:
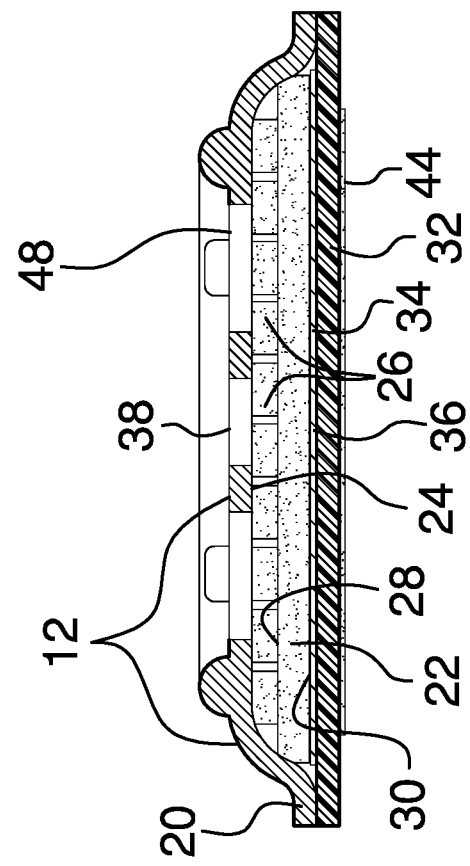
FIG. 5 is a cross-sectional view of an embodiment of the disclosure.

As best illustrated in FIGS. 1 through 5, the magnetic panty liner assembly 10 generally comprises a first panel 12. The first panel 12 is flexible. The first panel 12 is substantially permeable to menstrual fluid. The first panel 12 is substantially elongated rectangularly shaped, hour-glass shaped, or the like. The first panel 12 has opposing ends 14 that are arcuate, as shown in FIG. 2. The first panel 12 comprises foam or the like.

A ridge 16 is coupled to and extends from an upper face 18 of the first panel 12. The ridge 16 is positioned proximate to a perimeter 20 of the first panel 12. The ridge 16 is substantially impermeable to menstrual fluid. The ridge 16 comprises plastic or the like.

A second panel 22 is coupled to a lower face 24 of the first panel 12. The second panel 22 is flexible. The second panel 22 is absorbent of menstrual fluid. The second panel 22 comprises rayon, cotton, or the like.

A plurality of cylinders 26 is coupled to and extends between the lower face 24 of the first panel 12 and a top surface 28 the second panel 22. The cylinders 26 are absorbent of menstrual fluid so that each cylinder 26 is configured to wick the menstrual fluid from the first panel 12 to the second panel 22. The cylinders 26 comprise rayon, cotton, or the like.

A third panel 32 is coupled to a bottom surface 30 of the second panel 22 and the perimeter 20 of the first panel 12. The second panel 22 is enclosed between the first panel 12 and the third panel 32. The third panel 32 is flexible. The third panel 32 is substantially impermeable to menstrual fluid. The third panel 32 comprises plastic or the like.

A plurality of magnets 34 is fixedly positioned between the third panel 32 and the second panel 22. The magnets 34 are configured to reduce pain from menstrual cramps. The plurality of magnets 34 comprises a strip 36 that is flexible and magnetic. The strip 36 is substantially rectangularly shaped.

A first slit 38 is positioned through the first panel 12. The first slit 38 is configured to allow flow of the menstrual fluid through the first slit 38. The second panel 22 is positioned to absorb the menstrual fluid. The first slit 38 extends from proximate to the opposing ends 14 of the first panel 12.

A coupler 40 is coupled to an exterior face 42 of the third panel 32. The coupler 40 is configured to couple the third panel 32 to an undergarment of a user to position the ridge 16 in abutment to the skin of the user to prevent leakage of the menstrual fluid between the first panel 12 and the skin. The coupler 40 comprises adhesive 44.

A second slit 46 is positioned through the first panel 12. The second slit 46 is perpendicular to and intersects the first slit 38. The second slit 46 is configured to allow flow of the menstrual fluid through the second slit 46. The second panel 22 is positioned to absorb the menstrual fluid. The second slit 46 is positioned substantially equally distant from the opposing ends 14 of the first panel 12.

A plurality of holes 48 is positioned through the first panel 12. The holes 48 are configured to the flow of the menstrual fluid through the holes 48. The second panel 22 is positioned to absorb the menstrual fluid. Each hole 48 is positioned between the first slit 38 and the ridge 16 so that the plurality of holes 48 is positioned in a pair of rows 50. The holes 48 are circularly shaped.

A plurality of extrusions 52 is coupled to and extends from the upper face 18 of the first panel 12. The extrusions 52 are configured to deter movement of the menstrual fluid along the upper face 18. Each extrusion 52 is cylindrically shaped and positioned proximate to an associated hole 48.

In use, the adhesive 44 that is positioned on the third panel 32 is configured to couple the third panel 32 to the undergarment of the user. The ridge 16 is positioned in abutment to the skin of the user to prevent leakage of the menstrual fluid between the first panel 12 and the skin. The first slit 38, the second slit 46, and the holes 48 are configured to allow the flow of the menstrual fluid through the first slit 38, the second slit 46, and the holes 48. The cylinders 26 are configured to wick the menstrual fluid from the first panel 12 to the second panel 22. The second panel 22 is positioned to absorb the menstrual fluid. The strip 36, which is magnetic, is configured to reduce pain from menstrual cramps.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. A magnetic panty liner assembly comprising:
a first panel, said first panel being flexible, said first panel being permeable to menstrual fluid;
a ridge coupled to and extending from an upper face of said first panel, said ridge being positioned around a perimeter of said first panel, said ridge being impermeable to menstrual fluid;
a second panel coupled to a lower face of said first panel, said second panel being flexible, said second panel being absorbent of menstrual fluid wherein said first panel is configured for flowing of the menstrual fluid through said first panel positioning said second panel for absorbing the menstrual fluid;
a coupler coupled to an exterior face of a third panel, said coupler being configured for coupling said third panel to an undergarment of a user, said coupler comprising adhesive;
said third panel being coupled to a bottom surface of said second panel and said perimeter of said first panel such that said second panel is enclosed between said first panel and said third panel, said third panel being flexible, said third panel being impermeable to menstrual fluid wherein said coupler is positioned on said third panel such that said coupler is configured for coupling said third panel to the undergarment of the user positioning said ridge in abutment to skin of the user for preventing leakage of the menstrual fluid between said first panel and the skin; and
a plurality of magnets fixedly positioned between said third panel and said second panel wherein said magnets are configured for reducing pain from menstrual cramps;
a plurality of holes positioned through said first panel, wherein said holes are positioned in said first panel such that said holes are configured for the flowing of the menstrual fluid through said holes for absorbing the menstrual fluid in said second panel; and
a plurality of extrusions coupled to and extending from said upper face of said first panel wherein said extrusions are configured for deterring movement of the menstrual fluid along said upper face, each said extrusion being positioned at an associated said hole.

2. The assembly of claim 1, further including a first slit positioned through said first panel, wherein said first slit is positioned in said first panel such that said first slit is configured for flowing of the menstrual fluid through said first slit positioning said second panel for absorbing the menstrual fluid.

3. The assembly of claim 2, further including said first slit extending extending lengthwise along said first panel.

4. The assembly of claim 3, further including a second slit positioned through said first panel, said second slit being perpendicular to and intersecting said first slit, wherein said second slit is positioned in said first panel such that said second slit is configured for the flowing of the menstrual fluid through said second slit positioning said second panel for absorbing the menstrual fluid.

5. The assembly of claim 4, further including said second slit being positioned equally distant from said opposing ends of said first panel.

6. The assembly of claim 2, further including each said hole being positioned between said first slit and said ridge such that said plurality of holes is positioned in a pair of rows.

7. The assembly of claim 1, further including a plurality of cylinders coupled to and extending between said lower face of said first panel and a top surface of said second panel, said cylinders being absorbent of menstrual fluid, wherein said cylinders are positioned on said second panel such that each said cylinder is configured for wicking the menstrual fluid from said first panel to said second panel.

8. The assembly of claim 7, further comprising:
said first panel comprising foam;
said second panel and said cylinders comprising rayon; and
said ridge and said third panel comprising plastic.

9. The assembly of claim 8, further including said second panel and said cylinders comprising cotton.

10. The assembly of claim 1, further including said plurality of magnets comprising a strip, said strip being flexible, said strip being magnetic.

11. The assembly of claim 10, further including said strip being substantially rectangularly shaped.

12. The assembly of claim 1, further including said first panel being elongated rectangularly shaped.

13. The assembly of claim 1, further including said first panel having opposing ends, said opposing ends being arcuate.

14. The assembly of claim 1, further including said holes being circularly shaped.

15. The assembly of claim 1, further including each said extrusion being cylindrically shaped.

16. A magnetic panty liner assembly comprising:
a first panel, said first panel being flexible, said first panel being permeable to menstrual fluid, said first panel being elongated rectangularly shaped, said first panel having opposing ends, said opposing ends being arcuate, said first panel comprising foam;
a ridge coupled to and extending from an upper face of said first panel, said ridge being positioned to around a perimeter of said first panel, said ridge being impermeable to menstrual fluid, said ridge comprising plastic;
a second panel coupled to a lower face of said first panel, said second panel being flexible, said second panel being absorbent of menstrual fluid said second panel comprising rayon, said second panel comprising cotton;
a plurality of cylinders coupled to and extending between said lower face of said first panel and a top surface of said second panel, said cylinders being absorbent of menstrual fluid, wherein said cylinders are positioned on said second panel such that each said cylinder is configured for wicking the menstrual fluid from said first panel to said second panel;
a third panel coupled to a bottom surface of said second panel and said perimeter of said first panel such that said second panel is enclosed between said first panel and said third panel, said third panel being flexible, said third panel being impermeable to menstrual fluid, said third panel comprising plastic;
a plurality of magnets fixedly positioned between said third panel and said second panel, said plurality of magnets comprising a strip, said strip being flexible, said strip being magnetic, said strip being rectangularly shaped;
a first slit positioned through said first panel, wherein said first slit is positioned in said first panel such that said first slit is configured for flowing of the menstrual fluid through said first slit positioning said second panel for absorbing the menstrual fluid, said first slit extending extending lengthwise along said first panel;
a coupler coupled to an exterior face of said third panel, said coupler being configured for coupling said third panel to an undergarment of a user, wherein said coupler is positioned on said third panel such that said coupler is configured for coupling said third panel to the undergarment of the user positioning said ridge in abutment to the skin of the user for preventing leakage of the menstrual fluid between said first panel and the skin, such that said first slit is configured for flowing of the menstrual fluid through said first slit positioning said second panel for absorbing the menstrual fluid, such that said magnets are configured for reducing pain from menstrual cramps, said coupler comprising adhesive;
a second slit positioned through said first panel, said second slit being perpendicular to and intersecting said first slit, said second slit being positioned equally distant from said opposing ends of said first panel, wherein said second slit is positioned in said first panel such that said second slit is configured for the flowing of the menstrual fluid through said second slit positioning said second panel for absorbing the menstrual fluid;
a plurality of holes positioned through said first panel, wherein said holes are positioned in said first panel such that said holes are configured for the flowing of the menstrual fluid through said holes for absorbing the menstrual fluid in said second panel, each said hole being positioned between said first slit and said ridge such that said plurality of holes is positioned in a pair of rows, said holes being circularly shaped; and
a plurality of extrusions coupled to and extending from said upper face of said first panel wherein said extrusions are configured for deterring movement of the menstrual fluid along said upper face, each said extrusion being cylindrically shaped, each said extrusion being positioned at an associated said hole.

* * * * *